United States Patent
Xin et al.

(10) Patent No.: US 11,538,566 B2
(45) Date of Patent: *Dec. 27, 2022

(54) SAMPLE ANALYSIS WITH TEST DETERMINATION BASED ON IDENTIFIED CONDITION

(71) Applicant: Beckman Coulter, Inc., Brea, CA (US)

(72) Inventors: Rongchang Xin, Palmetto Bay, FL (US); Carlos A. Ramirez, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 1072 days.

This patent is subject to a terminal disclaimer.

(21) Appl. No.: 15/987,541

(22) Filed: May 23, 2018

(65) Prior Publication Data
US 2019/0362824 A1 Nov. 28, 2019

(51) Int. Cl.
G16H 15/00 (2018.01)
G16H 50/20 (2018.01)
G01N 33/569 (2006.01)
G01N 33/80 (2006.01)

(52) U.S. Cl.
CPC ....... *G16H 15/00* (2018.01); *G01N 33/56972* (2013.01); *G01N 33/80* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 5,125,737 A | 7/1992 | Rodriguez et al. | |
| 5,341,291 A * | 8/1994 | Roizen | G09B 7/04 600/300 |
| 5,529,933 A | 6/1996 | Young et al. | |
| 6,228,652 B1 | 5/2001 | Rodriguez et al. | |
| 7,109,036 B2 | 9/2006 | Ortiz et al. | |
| 7,135,341 B2 | 11/2006 | Ortiz et al. | |
| 7,176,031 B2 | 2/2007 | Li et al. | |
| 7,195,919 B2 | 3/2007 | Jacobs et al. | |
| 7,285,417 B2 | 10/2007 | Ortiz et al. | |
| 7,390,662 B2 | 6/2008 | Riley et al. | |
| 7,393,688 B2 | 7/2008 | Ortiz et al. | |
| 8,094,299 B2 | 1/2012 | Wells et al. | |
| 8,189,187 B2 | 5/2012 | Graham et al. | |
| 8,221,995 B2 | 7/2012 | Lee et al. | |
| 9,939,453 B2 | 4/2018 | Lu et al. | |
| 10,221,453 B2 | 3/2019 | Shi et al. | |
| 2009/0149724 A1 | 6/2009 | Mark et al. | |
| 2011/0076685 A1 | 3/2011 | Moeller et al. | |
| 2011/0166794 A1 | 7/2011 | Linssen et al. | |
| 2013/0197943 A1 | 8/2013 | Conlin et al. | |
| 2019/0128906 A1 | 5/2019 | Ramirez et al. | |
| 2019/0324035 A1 | 10/2019 | Magari et al. | |
| 2019/0324036 A1 | 10/2019 | Xin et al. | |
| 2019/0348182 A1 | 11/2019 | Magari et al. | |
| 2019/0383800 A1 | 12/2019 | Careaga et al. | |
| 2020/0243171 A1 | 7/2020 | Schmidt | |
| 2021/0007675 A1 | 1/2021 | Tejidor et al. | |
| 2021/0010924 A1 | 1/2021 | Tejidor et al. | |
| 2021/0011005 A1 | 1/2021 | Tejidor et al. | |

FOREIGN PATENT DOCUMENTS

| | | |
|---|---|---|
| EP | 1021701 | 7/2000 |
| EP | 1718966 | 11/2006 |
| WO | WO 88/07198 A1 | 9/1988 |
| WO | WO 2004/044556 A2 | 5/2004 |
| WO | WO 2012/139047 A2 | 10/2012 |
| WO | WO 2014/028534 A2 | 2/2014 |
| WO | WO 2014/084930 A1 | 6/2014 |
| WO | WO 2019/028448 | 2/2019 |

OTHER PUBLICATIONS

Petrak, RM, et al. "The value of an infectious diseases specialist." Clinical infectious diseases 36.8 (2003): 1013-1017.*
Nachimuthu, Senthil K., and Peter J. Haug. "Early detection of sepsis in the emergency department using Dynamic Bayesian Networks." AMIA Annual Symposium Proceedings. vol. 2012. American Medical Informatics Association, 2012.*
Chaves, Fernando, Bethany Tierno, and Dongsheng Xu. "Neutrophil volume distribution width: a new automated hematologic parameter for acute infection." Archives of pathology & laboratory medicine 130.3 (2006): 378-380.*
Coulter, "Coulter® 3-D VCS Technology," downloaded Feb. 11, 2022 from (http://www.cyto.purdue.edu/cdroms/cyto2/6/coulter/ss000125.htm), Beckman Coulter, Inc., Fullerton, CA, 3 pages, 1996.*
Aird, William C., "The Hematologic System as a Marker of Organ Dysfunction in Sepsis", Mayo Clin Proc., Jul. 2003;78:869-881, 2003 Mayo Foundation for Medical Education and Research.
Anonymous, "Multiple Logistic Regression Analysis", Jan. 17, 2013, retrieved from http://sphweb.bumc.cu.edu/otlt/MPH-Modules/8S/8S704_Multivariable/8S704_Multivariables8.html.
Bhargava, et al. "Elevated mean neutrophil volume+ CRP is a highly sensitive and specific predictor of neonatal sepsis", Letter to the Editor, International Journal of Laboratory Hematology, DOI 10.1111/iijh.12120, 2013, 4 pages.
"Biomarker," The Pharmaceutical Society of Japan, a pharmaceutical science glossary, 2008, 2 pgs.
Celik, et al., "Automated determination of neutrophil VCS parameters in diagnosis and treatment efficacy of neonatal sepsis", Pediatric Research, vol. 71, No. 1, Jan. 2012, pp. 121-125.
Chaves, et al. "Neutrophil Volume Distribution Width: A New Automated Hematologic Parameter for Acute Infection", Arch Pathol Lab Med, vol. 130. Mar. 2006, pp. 378-380.

(Continued)

*Primary Examiner* — G Steven Vanni
(74) *Attorney, Agent, or Firm* — Frost Brown Todd LLC

(57) ABSTRACT

It is possible that an analyzer may be operated such that it may perform tests to identify the presence or absence of a specified condition. Such tests may be performed using behaviors which are specific to the specified condition, and the results of those tests may be presented in a single output.

17 Claims, 1 Drawing Sheet

(56) References Cited

OTHER PUBLICATIONS

Chaves, et al. Quantitative Determination of Neutrophil VCS Parameters by the Coulter Automated Hematology Analyzer: New and Reliable Indicators for Acute Bacterial Infection. American Journal Clinical Pathology, 2005, 124:440-444.
Cho, et al., "Biomarkers of Sepsis", Infection & Chemotherapy, Feb. 2014; 46:1-12.
Crouser, et al, "Improved Early Detection of Sepsis in the ED with a Novel Monocyte Distribution Width Biomarker", 152#3 Chest, Sep. 2017, pp. 518-526.
Dellinger, et al. "Surviving Sepsis Campaign: International Guidelines for Management of Severe Sepsis and Septic Shock, 2012", Intensive Care Medicine, 2013, 39:164-228.
Dilmoula, et al., "Volume, Conductivity and Scatter Properties of Leukocytes (VCS Technology) in Detecting Sepsis in Critically Ill Adult Patients", Blood (ASH annual Meeting Abstracts) 2011; 118: Abstract 4729, 3 pages.
Early Sepsis Indicator Application Addendum UniCel DxH 900 Coulter Cellular Analysis System, Beckman Coulter, published Version: v1, Available online at: https://www.analis.be/site/objects/media/0/0/8/1/9/0081990_media/media1.pdf, Apr. 26, 2018, 38 pages.
Ferrer, et al., "Emperic Antibiotic Treatment Reduces Mortality in Severe Sepsis and Septic Shock from the First Hour: Results from a Guideline-Based Performance Improvement Program", Critical Care Medicine, Aug. 2014, vol. 42, No. 8, pp. 1749-1755.
Gaieski, et al., "Impact of time to antibiotics on survival in patients with severe sepsis or septic shock in whom early goal-directed therapy was initiated in the emergency department", Critical Care Medicine, 2010, vol. 38, No. 4, pp. 1045-1053.
Garnacho-Monterd, et al., "Impact of adequate empirical antibiotic therapy on the outcome of patients admitted to the intensive care unit with sepsis", Critical Care Medicine, 2003;31 :2742-51.
Gea-Banecloche, et al. "Sepsis associated with immunosuppressive medications: An evidence-based review" Critical Care Medicine 2004; 32:S578-S590.
Glickman, et al., Disease Progression in Hemodynamically Stable Patients Presenting to the Emergency Department with Sepsis. Academic Emergency Medicine, vol. 17, Issue 4, Apr. 2, 2010, pp. 383-390.
Goyette, et al., "Hematologic changes in sepsis and their therapeutic implications," Seminars in Respiratoiy and Critical Care Medicine, vol. 25, No. 6, pp. 645-659 (2004).
Hou, et al., Viral infection triggers rapid differentiation of human blood monocytes into dendritic cells, Blood, Mar. 29, 2012, vol. 119, No. 12, pp. 3128-3132.
Kaukonen, et al., "Systemic Inflammatory Response Syndrome Criteria in Defining Severe Sepsis," New England Journal of Medicine, 372: 1629-38, Apr. 23, 2015, (doi:610.1056/NEJMoal415236).
Lee, et al., "Mean cell volumes of neutrophils and monocytes are promising markers of sepsis in elderly patients", Blood Research, vol. 48, No. 3, Sep. 2013, 5 pages.
Levy, et al., "2001 SCCM/ESICM/ACCP/ATS/SIS Sepsis Definitions Conference", Critical Care Medicine, Mar. 28, 2003, 29: 530-538.
Liu, et al., "Hospital Deaths in Patients with Sepsis from 2 Independent Cohorts", JAMA Jul. 2, 2014; 312: 90-92.
Mardi, et al., Mean cell volume of neutrophils and monocytes compared with C-reactive protein, interleukin-6 and white blood cell count for prediction of sepsis and nonsystemic bacterial infections, accepted for publication, Sep. 23, 2009, International Journal of Laboratory Hematology 2010;32:410-418.
Park, et al, "Screening of sepsis using leukocyte cell population data from the Coulter automatic blood cell analyzer DxH800", International Journal of Laboratory Hematology, Dec. 6, 2010, 9 pages.
Raimondi, et al., "Automated Determination of Neutrophil Volume as Screening Test for Late-Onset Sepsis in Very Low Birth Infants", Pediatric Infectious Disease Journal, Feb. 2010; 29:288-89.
"Red Blood Cell Distribution With (RDW): Definition and Calculation—LabCE.com, Laboratory Continuing Education," Nov. 2012, downloaded Aug. 22, 2019 from: https://labce.com/spg579122_red_blood_cell_distribution_width_rdw_definition_a.aspx , 1 pg.
Seymour, et al. "Severe Sepsis in Pre-Hospital Emergency Care: Analysis of Incidence, Care, and Outcome", American Journal of Respiratory Critical Care Medicine, Dec. 15, 2012; 186:1264-71.
Shalova, et al., "Human Monocytes Undergo Functional Reprogramming during Sepsis Mediated by Hypozia-Inducible Factor-1a", Immunity, Mar. 17, 2015; 42:484-98.
Singer, et al., "The Third International Consensus Definitions for Sepsis and Septic Shock (Sepsis-3)," JAMA, 10 315(8): 801-810, Feb. 23, 2016.
Skibsted, et al., "Bench-to-bedside review: Future novel diagnostics for sepsis-13 a systems biology approach", Critical Care Oct. 4, 2013; 17:231, 15 pages.
Sukhacheva, et al., "The Role of Monocytes in the Progression of Sepsis," Beckman Coulter, 2018, downloaded Aug. 22, 2019 from: media.beckmancoulter.com/-/media/diagnostics/products/hematology/early-sepsis-indicator/docs/role-of-monocytes-for-progression-of-sepsis-en.pdf, 12 pgs.
Torio, et al., "National Inpatient Hospital Costs: The Most Expensive Conditions by Payer, 2011", H-CUP US, Aug. 2013, 8 pages, retrieved from: https://www.hcup-us.ahrq.gov/reports/statbriefs/sb160.jsp.
"UniCel DxH 800—Coulter Cellular Analysis System", Available online at: https://www.udh.med.sa/advices/DxH_operator_Manual.pdf, Aug. 5, 2017, 54 pages.
Vis, et al., "Verification and Quality Control of Routine Hematology Analyzers", International Journal of Laboratory Hematology, vol. 38, No. 1, May 9, 2016, pp. 100-109.
Warner, "Tips for evaluating a peripheral blood smear for possible sepsis," Jan. 15, 2013, 3 pages, available at laboratorian.advanceweb.com/signs-of-sepsis/.
Zhou, et al., "VCS parameters of neutrophils, monocytes and lymphocytes may indicate local bacterial infection in cancer patients who accepted cytotoxic chemotherapeutics," Eur J Clin Microbiol Infect Dis, 2016, 35:41-48, 8 pgs.
Zonneveld, R., et al., "Analyzing Neutrophil Morphology, Mechanics, and Motility in Sepsis: Options and Challenges for Novel Bedside Technologies," Crit Care Med, 2016, 44(1):218-228, 11 pgs.
European Examination Report dated Oct. 15, 2020 for Application No. EP 17704357.7, 10 pgs.
International Search Report and Written Opinion dated Apr. 20, 2017 for International Application No. PCT/US2017/014708, 16 pages.
International Search Report and Written Opinion dated May 4, 2018 for International Application No. PCT/US2018/020087, 13 pages.
International Search Report and Written Opinion dated Mar. 26, 2019 for International Application No. PCT/US2018/057645, 16 pages.
International Search Report and Written Opinion dated Sep. 4, 2019 for International Application No. PCT/US2019/028486, 11 pgs.
International Search Report and Written Opinion dated Aug. 2, 2019 for International Application No. PCT/US2019/028487, 7 pages.
International Search Report and Written Opinion dated Aug. 23, 2019 for International Application No. PCT/US2019/028488, 10 pgs.
International Search Report and Written Opinion dated Aug. 20, 2019 for International Application No. PCT/US2019/031151, 9 pages.
International Search Report and Written Opinion dated Oct. 20, 2020 for International Application No. PCT/US2020/041535, 12 pgs.
International Search Report and Written Opinion dated Oct. 8, 2020 for International Application No. PCT/US2020/041548, 10 pgs.
International Search Report and Written Opinion dated Oct. 5, 2020 for International Application No. PCT/US2020/041541, 10 pgs.
Japanese Office Action, Notice of Reasons for Refusal, dated Oct. 29, 2020 JP 2018-538892, 27 pgs.

(56) References Cited

OTHER PUBLICATIONS

U.S. Office Action, Non-Final Rejection, dated Jul. 31, 2020 for U.S. Appl. No. 16/073,757, 23 pgs.
U.S. Office Action, Notice of Allowance, dated Feb. 8, 2021 for U.S. Appl. No. 16/073,757, 20 pgs.

* cited by examiner

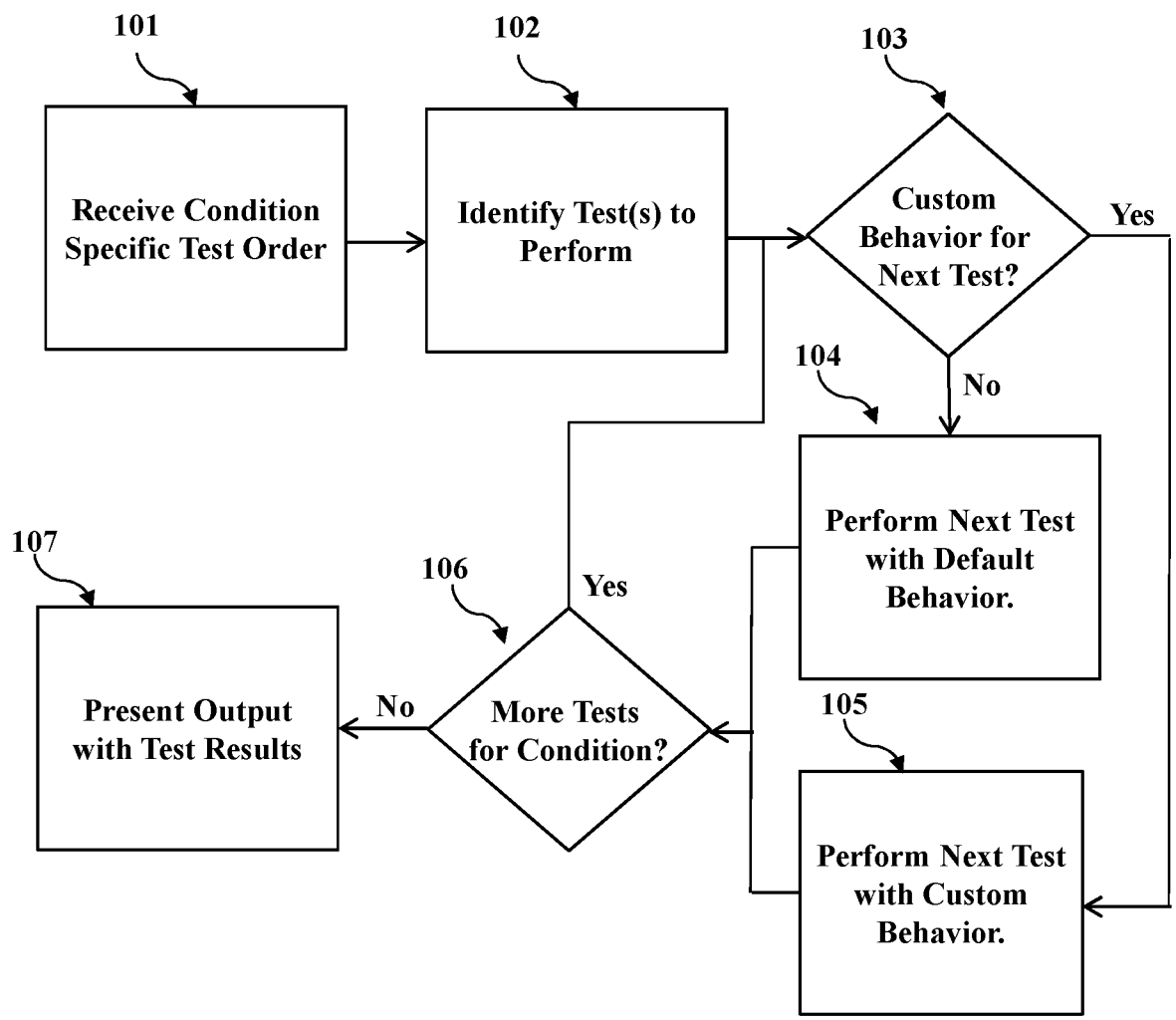

SAMPLE ANALYSIS WITH TEST DETERMINATION BASED ON IDENTIFIED CONDITION

FIELD

The disclosed technology pertains to analyzing samples on laboratory instruments.

BACKGROUND

Often, when blood or another body fluid is analyzed, it may be subjected to tests that are specified to identify various parameters or biomarkers. However, it is possible that simply specifying parameters to be measured may provide suboptimal results in some cases. For example, in the context of health condition diagnosis and treatment, it is possible that a single parameter may be relevant to the treatment and/or diagnosis of multiple conditions, including some conditions that would benefit from measurements having a level of accuracy that would be pointless for other conditions. Additionally, in some cases, tests may be organized, and test results may be reported based on particular types of parameters (e.g., cell types), but it is possible that a sample may be collected and/or analyzed for a purpose that would benefit from consideration of information related to multiple types of parameters. This can cause various problems, such as making it more difficult to obtain information relevant to a particular analytic goal and/or rendering analysis less efficient in cases where tests for a parameter are keyed to more demanding requirements than may be appropriate for a particular use.

SUMMARY

There is a need for improved technology for analyzing samples in a manner that is consistent with specific analytic goals. It may thus be an object of some embodiments to provide a method that could comprise steps such as receiving an order identifying a condition that one or more tests should be performed to detect, determining the one or more tests to perform to detect the condition, determining a set of custom behaviors to use in performing that test and obtaining a result for that test by performing it using the custom behaviors, and presenting the results for the one or more tests performed to detect the condition. In some embodiments, this objective may be fulfilled by the subject matter of the independent claims, wherein further embodiments are incorporated in the dependent claims.

BRIEF DESCRIPTION OF THE DRAWINGS

The drawings and detailed description that follow are intended to be merely illustrative and are not intended to limit the scope of the invention as contemplated by the inventors.

FIG. 1 presents an exemplary process that may be used in some embodiments to control and/or present results of tests on a condition specific basis.

DETAILED DESCRIPTION

In light of the above, it could be beneficial to be able to automatically customize the analysis of samples based on specific objectives that analysis is intended to or could be expected to advance. According to a first aspect, some embodiments may include a method comprising steps such as receiving an order identifying a condition that one or more tests should be performed to detect, determining the one or more tests to perform to detect the condition, determining a set of custom behaviors to use in performing that test and obtaining a result for that test by performing it using the custom behaviors, and presenting the results for the one or more tests performed to detect the condition.

In some embodiments according to the first aspect, the one or more tests to perform to detect the condition may comprise a first test comprised by a first panel and a second test comprised by a second panel. In such embodiments, the results for the one or more tests performed to detect the condition may be simultaneously presented in a single output.

In some embodiments according to the first aspect, there may be a first test to perform to detect the condition that is performed on an analyzer having a default data collection requirement, and the set of custom behaviors may comprise a custom data requirement for the first test. In some embodiments of this type, the condition may be a condition that needs to be detected at an early state, for example in a certain embodiment this may be sepsis, the default data collection requirement for the first test may be acquiring between 500 and 1,000 monocytes, and the extended data collection requirement for the first test may be acquiring a higher number of monocytes (e.g., between 1,000 and 2,000, between 4,000 and 5,000, etc.). Additionally, in other embodiments, various other parameters may be used to detect a condition at an early state or even before a condition can be identified. Similarly, in some embodiments such as described initially in this paragraph, the one or more tests to perform to detect the condition may comprise a second test, and the set of custom behaviors to use in performing the second test may be no custom behaviors.

In some embodiments according to the first aspect, the method may comprise, using an index calculation function, calculating a value indicating a likelihood that the condition identified in the order is present. Such an embodiment may also comprise presenting the value indicating the likelihood that the condition identified in the order is present. Similarly, in some embodiments of this type, the index calculation function for a condition identified in an order may be a function that calculates a value indicating the likelihood that the condition is present based on a predefined set of parameters. In some embodiments parameters may be the following but not limited to distribution width associated with various measurable parameters associated with the patient sample, ratios between various measurable parameters associated with the patient sample etc. Similarly, in some embodiments such as described initially in this paragraph, a computer performing the method may be communicatively connected to a remotely located server and may also be configured to receive an updated index calculation function.

In some embodiments according to the first aspect, the one or more tests to perform to detect the condition may comprise a first test and a second test, where the first test is a test of a white blood cell parameter and the second test may be a test of a red blood cell parameter. Additionally, in some embodiments of this type the first test and the second test may be performed using reagents on a single panel.

Corresponding systems comprising one or more computers configured by computer executable instructions stored on non-transitory computer readable media to perform steps of methods described in any of the preceding embodiments, as well as non-transitory computer readable media storing instructions for performing steps of method described in any of the preceding embodiments, could also be implemented without undue experimentation by those of ordinary skill in the art based on this disclosure. Similarly, the disclosed technology may be used in the detection of a variety of clinical conditions, such as sepsis, malaria, dengue, anemia, leukemia, etc. Accordingly, the preceding description of potential embodiments and aspects, as well as the discussion of illustrative embodiments set forth herein, should be understood as being illustrative only, and should not be treated as limiting.

Turning now to FIG. 1, FIG. 1 presents an exemplary process that may be used in some embodiments to control and/or present results of tests on a condition specific basis. Initially, in the process of FIG. 1, an order will be received 101 for testing for a specific condition. Preferably, this will step (as well as the other steps from the process of FIG. 1) will be performed by a computer controlling a piece of laboratory equipment (e.g., a hematology analyzer) that would perform tests for detecting the relevant condition. In embodiments where a process such as illustrated in FIG. 1 is performed by a computer, the step of receiving 101 a condition specific test order could be performed in a variety of manners. For example, in some embodiments, a computer may be configured to receive 101 an order for testing for a specific condition when a physician specifies that tests for that condition should be run on a sample. Such an order may, in some embodiments, be transmitted electronically to the analyzer, while in other embodiments an analyzer implemented based on this disclosure may be configured to include specific conditions in a menu presented to an operator and to allow that operator to use that menu to specify the condition. In yet other embodiments, a computer may be configured to automatically generate an order to test a sample for a condition. For example, the computer may be configured with rules (such as those described in co-pending PCT application PCT/US18/20087 for a Cross Discipline Disease Management System, the disclosure of which is hereby incorporated by reference in its entirety) for triggering a reflex test for a specific condition when it appears that there is a heightened likelihood that that condition is present. Combinations may also be possible. For example, in some embodiments, a computer may be configured to be able to receive 101 an order for testing a specific condition both when it is directly requested by a physician, and when it is automatically generated.

In the process of FIG. 1, once a condition specific test order has been received 101, the process continues with identifying 102 the test(s) to perform for that condition. As with receiving 101 the condition specific test order, the step of identifying 102 test(s) for the specified condition may be performed in a variety of different ways. For example, in some embodiments, a computer performing a method such as shown in FIG. 1 may have stored, either in its own memory or in a local database, data (e.g., in one or more tables) correlating particular conditions with particular test(s) that would be relevant to the identification of those conditions. In such an embodiment, the step of identifying 102 the test(s) to perform may be done by the computer retrieving the test(s) from its own memory or local database by running a query using the condition specified in the previously received 101 order. In other embodiments, a computer performing a process such as shown in FIG. 1 may query a remote database (e.g., a database hosted on a cloud server) to identify 102 what test(s) should be performed, or may attempt to query a remote database and, if such a query fails (e.g., if there is a problem communicating with the remote database) fall back on whatever information is stored in the computer's memory or in a local database.

Other alternatives may also be possible. For example, in some embodiments, a condition specific test order may specify both the test(s) to perform and the condition which the test(s) are intended to detect. In this type of scenario, a computer performing a process such as shown in FIG. 1 may simply identify 102 the test(s) to perform as the test(s) specified in the order itself, or may identify 102 the test(s) as the test(s) specified in the order plus any additional test(s) that may be indicated by information stored in a local or remote database. Additional variations (e.g., identifying test(s) specified in an order as the test(s) to be performed, with any additional test(s) indicated by information in a local or remote database being treated as possible reflex test(s) in case the test(s) specified in the order were inconclusive) may also be possible in some embodiments. Accordingly, the discussion above of identifying 102 test(s) to be performed, like the discussion of receiving 101 a condition specific test order, should be understood as being illustrative only, and should not be treated as limiting on the scope of any claims in this document or any other document claiming the benefit of this disclosure.

After identification 102 of the test(s) to be performed, the process of FIG. 1 continues with a determination 103 of whether there are custom behaviors for the next test (which, if this is the first time the determination 103 had been performed for a sample, would be the first test identified for the condition). To illustrate what this type of determination might entail, consider the case where the received 101 order is to test a sample to determine whether the individual from whom that sample was collected is suffering from sepsis, and the identified 102 test(s) to perform on that sample included determining monocyte distribution width (MDW). Consider also the hypothetical situation in which such an order is to be processed using an instrument having a default behavior for determining MDW that includes a number of monocytes to detect in a sample. In this type of hypothetical scenario, the step of determining 103 whether there is custom behavior for the sample may include determining that, because the sample is being run to detect sepsis, the data collection should be extended such that the default behavior would be overridden and data for a larger number of monocytes would be acquired, thereby allowing for a more precise MDW determination of a type that may be appropriate for testing for sepsis but that may not be necessary for other purposes.

In some embodiments following this type of hypothetical scenario, the default behavior for determining MDW may be detection of between 500 and 1,000 monocytes, while the custom behavior may be acquiring data for between 1,000 and 2,000 monocytes. In other embodiments, the custom behavior may be acquiring data for between 4,000 and 5,000 monocytes. In other embodiments, different types of custom behaviors may be implemented. Accordingly, the discussion above of specific custom behaviors should be understood as being illustrative only, and should not be treated as limiting.

With respect to execution, the determination 103 of whether there are custom behaviors for a test could be performed in manners similar to those discussed previously for the identification 102 of tests to perform. Thus, in some embodiments, whether there is custom behavior for a test could be determined 103 by a computer performing a query of its own memory of a local database using the relevant test and condition, and use the result of that query to define the custom behavior (if any) for that test. Similarly, in some embodiments, whether there is custom behavior for a test could be determined 103 by querying a remote database and/or by reference to the condition specific testing order (e.g., if the order had specified particular behaviors, such as extended data collection, to be used when performing particular test(s)). Accordingly, like the identification 102 of test(s), the determination 103 of custom behavior should be understood as potentially being susceptible to implementation in different manners, and the protection provided by this or any related document should not be limited to only embodiments in which that step is performed using one of the exemplary implementations described herein.

After the determination 103 had been made of whether there were custom behaviors for a test, that test could then be performed 104 with its default behaviors (if there were no custom behaviors for that test), or could be performed 105 with the custom behaviors (if it had been determined 103 that such custom behaviors existed). This could then repeat until all tests for the condition 106 from the condition specific test order had been performed. Finally, the results of the tests could be presented 107. In some embodiments, this may be done, for example, by simply presenting the test results on a panel by panel basis and allowing the user to see the test results by selecting the panels in which the tests were contained. Alternatively, in some embodiments, all test results may be gathered into a single page so that they could be presented together regardless of whether the reagents for those tests had been included in different panels. For instance, in this type of embodiment, if tests performed on a sample had included a test performed with a reagent from a white blood cell panel and a test with a reagent from a red blood cell panel, then those results could be presented 107 together in a single interface despite the fact that the tests had been in (i.e., had relied on reagents from) different panels. Additionally, some embodiments of aspects of the disclosed technology may allow analyzers that do not include code for gathering results of tests from multiple panels in a single output to provide condition specific unified output through the use of condition specific panels. That is, in some embodiments a panel may be provided which is organized to include the reagents for tests that would be used to detect a particular condition, rather than to include reagents for tests on a particular type of subject matter (e.g., red blood cell or white blood cell panels).

Further variations on the presentation 107 of results may also be possible in some embodiments. For example, in some embodiments, prior to the presentation of results, the data gathered in the tests may be used to calculate a value reflecting how likely it is that the specified condition is present. This may be calculated, in some embodiments, using an equation of the general form index=f(parameter 1, parameter 2, . . . parameter n) to calculate a value illustrating the likelihood that a patent from whom a sample was taken has the relevant clinical condition based on the data collected regarding that sample.

In some embodiments, a computer in a laboratory that would perform an index calculation such as described above may be configured to communicate with a remote server to determine if the server had a model for calculating an index that was more recent than the computer's then current model and, if so, the computer could update to use the more current model for future index calculations. In embodiments where this type of updating is supported, it may also be used for upgrading data other than models used for calculating likelihood indices. For example, it is possible that, as additional research is done, a remote server may be updated to include data indicating new tests and/or custom behaviors that had been found to be useful in detecting various conditions, and this information may be propagated to local laboratory computers in a manner similar to that described for the index updates.

Further variations on, and features for, the inventors' technology will be immediately apparent to, and could be practiced without undue experimentation by, those of ordinary skill in the art in light of this disclosure. Accordingly, instead of limiting the protection accorded by this document, or by any document which is related to this document, to the material explicitly disclosed herein, the protection should be understood to be defined by the claims, if any, set forth herein or in the relevant related document when the terms in those claims which are listed below under the label "Explicit Definitions" are given the explicit definitions set forth therein, and the remaining terms are given their broadest reasonable interpretation as shown by a general purpose dictionary. To the extent that the interpretation which would be given to such claims based on the above disclosure is in any way narrower than the interpretation which would be given based on the "Explicit Definitions" and the broadest reasonable interpretation as provided by a general purpose dictionary, the interpretation provided by the "Explicit Definitions" and broadest reasonable interpretation as provided by a general purpose dictionary shall control, and the inconsistent usage of terms in the specification or priority documents shall have no effect.

Explicit Definitions

When appearing in the claims, a statement that something is "based on" something else should be understood to mean that something is determined at least in part by the thing that it is indicated as being "based on." When something is required to be completely determined by a thing, it will be described as being "based exclusively on" the thing.

When used in the claims, "determining" should be understood to refer generating, selecting, defining, calculating or otherwise specifying something. For example, to obtain an output as the result of analysis would be an example of "determining" that output. As a second example, to choose a response from a list of possible responses would be a method of "determining" a response. As a third example, to identify data received from an external source (e.g., a microphone) as being a thing would be an example of "determining" the thing.

When used in the claims a "means for determining one or more tests and test performance behaviors to detect a specified condition" should be understood as a means plus function limitation as provided for in 35 U.S.C. § 112(f), in which the function is "determining one or more tests and test performance behaviors to detect a specified condition" and the corresponding structure is a computer configured to perform processes as illustrated in FIG. 1 and described in the corresponding text.

The invention claimed is:

1. A method for performing condition specific testing on a biological sample, the method performed by a computer and an analyzer controlled by the computer and configured to perform a plurality of tests, the method comprising:
   a) receiving the biological sample and an order associated with the biological sample identifying a condition;
   b) determining one or more tests from the plurality of tests based on the condition identified in the order;
   c) for each of the one or more tests, obtaining a result for that test by performing that test on the received biological sample; and
   d) presenting the results for the one or more tests;

wherein:
A) the method comprises calculating a value indicating a likelihood that the condition identified in the order is present; and
B) presenting the results for the one or more tests further comprises presenting the value indicating the likelihood that the condition identified in the order is present.

2. The method of claim 1, wherein:
a) the one or more tests comprise:
   i) a first test comprised by a first panel; and
   ii) a second test comprised by a second panel; and
b) the method comprises presenting the results for the one or more tests simultaneously in a single output.

3. The method of claim 1, wherein:
a) the method comprises, for each test from the one or more tests, determining a set of custom behaviors to use in performing that test based on the condition; and
b) for a first test from the one or more tests:
   i) that test is performed on the analyzer, and the analyzer has a default data collection requirement for that test; and
   ii) the set of custom behaviors for that test comprises an extended data collection requirement which exceeds the default data collection requirement for that test.

4. The method of claim 3, wherein:
a) the one or more tests comprise a second test; and
b) the set of custom behaviors to use in performing the second test is no custom behaviors.

5. The method of claim 1 wherein the computer is communicatively connected to a server and is configured to receive an updated index calculation function.

6. The method of claim 1 wherein:
a) the one or more tests comprise a first test and a second test;
b) the first test is a test of a white blood cell parameter;
c) the second test is a test of a red blood cell parameter; and
d) the first test and the second test are performed using reagents on a single panel.

7. The method of claim 6, wherein the single panel is a condition specific panel corresponding to the condition identified in the order.

8. The method of claim 1, wherein the analyzer is a hematology analyzer, and the biological sample is a blood sample.

9. A system comprising an analyzer configured to perform a plurality of tests controlled by one or more computers configured by computer executable instructions stored on a non-transitory computer readable medium to perform steps comprising:
a) receiving an order identifying a condition that one or more tests should be performed to detect;
b) determining the one or more tests from the plurality of tests to perform to detect the condition;
c) for each of the one or more tests to perform to detect the condition, obtaining a result for that test by causing the analyzer to perform that test;
d) calculating a value indicating a likelihood that the condition identified in the order is present; and
e) presenting the results for the one or more tests performed to detect the condition by performing acts comprising presenting the value indicating the likelihood that the condition identified in the order is present.

10. The system of claim 9, wherein:
a) the one or more tests to perform to detect the condition comprises:
   i) a first test comprised by a first panel; and
   ii) a second test comprised by a second panel; and
b) presenting the results for the one or more tests performed to detect the condition simultaneously in a single output.

11. The system of claim 9, wherein the steps comprise:
a) for each of the one or more tests to perform to detect the condition, determining a set of custom behaviors to use in performing that test; and
b) for a first test from the one or more tests to perform to detect the condition, performing that test comprises overriding a default data collection requirement for that test and using an extended data collection requirement for that test.

12. The system of claim 11, wherein:
a) the one or more tests to perform to detect the condition comprises a second test; and
b) the set of custom behaviors to use in performing the second test to detect the condition is no custom behaviors.

13. The system of claim 9, wherein the computer is configured to, using an index calculation function, calculate the value indicating the likelihood that the condition identified in the order is present.

14. The system of claim 13 wherein the computer is communicatively connected to a server and is configured to receive an updated index calculation function.

15. The system of claim 9 wherein:
a) the one or more tests to perform to detect the condition comprises a first test and a second test;
b) the first test is a test of a white blood cell parameter;
c) the second test is a test of a red blood cell parameter; and
d) the system comprises a panel comprising reagents for performing the first test and reagents for performing the second test.

16. The system of claim 15, wherein the panel comprising reagents for performing the first test and reagents for performing the second test is a condition specific panel corresponding to the condition identified in the order.

17. The system of claim 9, wherein the analyzer is a hematology analyzer, and wherein, for each of the one or more tests to perform to detect the condition, causing the analyzer to perform that test comprises causing the analyzer to perform that test on a previously received blood sample.

* * * * *